United States Patent [19]

Weinreb

[11] Patent Number: 4,760,092

[45] Date of Patent: Jul. 26, 1988

[54] TREATMENT OF DEMYELINATING DISEASES

[75] Inventor: Herman J. Weinreb, New York, N.Y.

[73] Assignee: The Rockefeller University, New York, N.Y.

[21] Appl. No.: 937,436

[22] Filed: Dec. 3, 1986

Related U.S. Application Data

[63] Continuation of Ser. No. 792,610, Oct. 29, 1985, abandoned.

[51] Int. Cl.⁴ ............................................. A61K 31/165
[52] U.S. Cl. ..................................................... 514/617
[58] Field of Search ................................ 514/613, 617

[56] References Cited

PUBLICATIONS

Horrobin et al., British Med. Journal Jan. 20, 1979 (BMJ).

*Primary Examiner*—Stanley J. Friedman
*Attorney, Agent, or Firm*—Wyatt, Gerber, Shoup and Badie

[57] ABSTRACT

Method of treating demyelinating diseases such as multiple sclerosis by treatment with colchicine or colchiceine.

3 Claims, No Drawings

TREATMENT OF DEMYELINATING DISEASES

CONTINUING DATA

This application is a continuation of Ser. No. 792,610, filed Oct. 29, 1985 and now abandoned.

FIELD OF THE INVENTION

This invention relates to the treatment of demyelinating diseases, particularly multiple sclerosis (MS), with colchicine or colchiceine.

BACKGROUND OF THE INVENTION

Demyelinating diseases of central or peripheral origin are diseases which destroy myelin which is a substance compounded principally of fats and proteins. It is wrapped in numerous thin layers around nerve fibers where it acts as an insulator and speeds the transmission of messages along the nerve fibers. These afflictions include for example MS, GuillainBarre syndrome and polymyositis. Of these, MS is by far the most prevalent. This invention will be described principally as it relates to MS.

MS is a disease of profound suffering and pervasive disability, the etiology of which remains unknown despite intensive investigation. It consists of patches or plaques of damaged myelin scattered throughout the central nervous system resulting from demyelination and subsequent scar formation. The name "multiple sclerosis" describes the fact that in this disease there are many damaged areas filled with sclerotic (scar) tissue. Over a long period, new scar tissue may develop or old ones enlarge. The result is progressive degeneration of the nervous system resulting in progressive debilitation of the afflicted individual.

MS significantly affects the most productive human age group (20–40 yrs). There are close to a million victims in the United States alone. The chief consequence of the disease is increasing deterioration of neurological function. Most victims are confined to wheelchairs or bed after 10 years. The prevalence ranges from 50/100,000 in the United States to 200/100,000 in Canada, Northern Great Britain, parts of France, Scandinavia and Russia.

In the absence of a known cause for the disease, treatments have been empirical. The treatments can be divided principally into anti-inflammatory, immunosuppressive, anti-infective and biological response modifications. Additionally, a large number of miscellaneous treatments have been attempted. No satisfactory treatment of MS has yet been revealed.

ACTH has been of some benefit in promoting remission of acute attacks, but has not been shown to modify the overall course of the disease. Combination therapy with ACTH and cyclophosphamide have shown some promise in temporarily halting the progression of severe MS. However, the work is very recent, and no final conclusion has been possible.

Copolymer-I, a synthetic polypeptide resembling myelin basic protein has shown some benefit, but these results are also too recent for proper evaluation.

In 1982 the National Multiple Sclerosis Society published a booklet entitled Therapeutic Claims in Multiple Sclerosis (International Standard Book Number 0-9608098-0-5). In it more than twenty methods of treating MS ranging from diet control to a wide variety of therapeutic agents including, for example, anticoagulants, vasodilators, immunosuppressants, and protease inhibitors are discussed. The majority are characterized as ineffective, not recommended, or not sufficiently tested.

There is a need for a safe, reliable and effective method of treating MS and related diseases so as to retard their progression, particularly a treatment which will retard demyelination before the disease becomes disabling. It would be especially convenient if treatment could be accomplished by way of sustained release compositions which would decrease the number of separate dosage units required each day during treatment, thus improving compliance.

Colchicine is (S)-N-(5,6,7,9-tetrahydro-9-oxabenzo[a]heptaten-7-yl) acetamide. It has long been known as a therapeutic agent for humans, particularly as a gout suppressant and in the treatment of Familial Mediterranean Fever. It may be safely administered both orally and parenterally. Its activity in the mammalian body is well known and understood. Colchiceine is the 10-demethylated homolog of colchicine. It has also been used for the same purposes. Colchicine is the preferred therapeutic agent for the known utilities. It is also the preferred agent for use in this invention because it is readily available at reasonable cost and is extremely effective in retarding the progression of MS.

THE INVENTION

It has now been discovered that both colchicine and colchiceine may be administered to humans to treat demyelinating diseases, such as MS by retarding the process of demyelination. It is most convenient to administer the therapeutic agent orally, but parenteral administration including intravenous or intramuscular injection may also be employed.

An effective dose for treating the disease will vary with a number of factors well known and understood by the physician. These include, for example, age and weight of the patients and the status of the disease. An effective dose may vary from about 0.02 to 0.04 mg/kg of body weight per day. Most conveniently, the required dosage will be administered once a day in a sustained release dosage unit which may contain 1.2 to 2.4 mg of active compound as the principal active ingredient. Another convenient dosage unit is a scored tablet, each tablet containing 0.2 to 0.4 mg of active agent per scored segment. Such tablets are particularly useful since they permit the physician to investigate a large number of dosage regimens and titrate the optimum effective dosage for an individual patient.

It has been observed that dosage regimens appreciably below those suggested above are generally ineffective. Dosages appreciably above these values are not generally recommended for patients using colchicine or colchiceine for any purpose, because of undesirable side reactions, particularly diarrhea.

The oral and parenteral dosage units will be prepared in accordance with standard procedures and will contain the selected active compound as the only or principal active ingredient in the composition. Any of a wide variety of known inert excipients may be employed to prepare compositions useful in the practice of this invention. These include, for example, dextrose, starch, talc, various types of clay, mineral oil, cottonseed or sesame oil, as well as water or various miscible and immiscible aqueous compositions in which the therapeutic agent is soluble or may be suspended with the aid of known surfactants.

For buccal and sublingual administration the active ingredient can be formulated in tablet form with water soluble binding agents such as lactose or other palatable carbohydrates.

For rectal administration suppositories or inserts containing the active ingredient dispersed in such reagents as cocoa butter, petroleum, or other natural lubricants or in a synthetic emmollient such as polyethylene glycol 1000 or polyethylene glycol 4000 may be used.

Transdermal administration will normally be from a sustained release preparation which may be applied as a patch or from a gauze applied to the skin.

The preferred method of administering the active agents of this invention is from sustained release dosage forms since this is most convenient for patients, and avoids the necessity of constant clock watching or interruption of normal daily activities. A number of compositions suitable for such preparations are known and can be usefully employed.

One convenient procedure is to formulate the selected motility control agent in a time disintegrating tablet or pellet coated with various thicknesses of known materials such as carnauba wax, cellulose esters and ethers, fats, keratin, gluten or various natural or synthetic esters. Tablets in which the motility control agent is contained in a slowly dissolving core such as a core of stearic acid or castor oil are useful. Mixed release granule tablets comprising mixtures of the drug itself and the drug in separate particles coated with materials which dissolve at different rates such as dehydrogenated castor oil or fatty acids can also be employed. Alternatively the active material can be bound to an ion exchange resin such as a sulfuric acid type cation exchange resin.

It has been established that the active agents of this invention are useful in treating the diseases to which this disclosure applies by inhibiting demyelination, thereby abating the progression of neurological disability.

In one such test, 16 MS patients with chronic progressive MS were treated orally using tablets containing 0.6 mg of colchicine three times per day.

All patients met published criteria for clinically defined MS and had a chronic progressive disease profile at the time of testing in the independent opinion of two neurologists. The instruments for quantitating disease were the Standard neurological Exam (SNE), the Functional Status Scale (FSS), the Disability Status Scale (DSS), the Ambulation Index (AI) and the Upper Extremity Index (UEI). The definition of chronic progressive disease, the quantity of progression required, and the inclusion and exclusion criteria followed the standard, art accepted guidelines. Patients were obtained from a population being followed at The Rockefeller University Hospital (RUH) and from local referring physicians. Patients were hospitalized for up to two weeks at RUH, where baseline studies of their medical and neurologic status were performed, along with baseline laboratory studies including the CBC, ESR, SMA-6, SMA-12, UA, EKG, CXR, and stool guaiac. Lumbar punctures and studies of immune function were also performed.

Neurological assessments during the course of treatment were performed independently by two neurologists. After obtaining informed consent the patients began treatment and were evaluated at appropriate intervals to determine their status. Follow-up evaluation consisted of the history and physical exam, neurological exam as described by the above criteria and laboratory studies consisting of the CBC, ESR, SMA-6, SMA-12, UA and occult stool blood. Treatment failure was defined as a decline in either the DSS or the AI/UEI by one point or the FSS by two points for a period of one month after beginning colchicine.

The results are shown in the following Table.

TABLE

| Patient/Age/Sex | Duration of Disease (yrs) | Disability Status* | Ambulation Index* | Followup (mos) |
|---|---|---|---|---|
| FRCA/41/M | 3 | 6A | 5 | 12 |
| JOFE/42/M | 15 | 6B | 6 | 10 |
| ALDE/34/M | 5 | 6A | 4 | 9 |
| MAAD/46/F | 10 | 6B | 6 | 9 |
| BAFR/42/F | 3 | 2 | 2 | 8 |
| VIKU/32/F | 1 | 2 | 2 | 7 |
| SUPE/43/F | 9 | 3 | 2 | 7 |
| EPLI/61/M | 30 | 6A | 4 | 6 |
| WAJA/35/M | 7 | 6B | 6 | 5 |
| POFA/39/F | 20 | 6B | 6 | 5 |
| JOST/24/F | 2 | 2 | 2 | 5 |
| MAJO/45/F | 16 | 7 | 7 | 4 |
| ROEH/55/M | 23 | 6A | 4 | 4 |
| JOCA/52/M | 25 | 6A | 4 | 4 |
| HIHE/56/F | 1 | 3 | 3 | 4 |
| RIPR/47/M | 15 | 6A | 5 | 4 |

*As proposed by Weiner et al (N Engl. J. Med 1983; 308: 173–80)

The integers in the columns under Disability Status and Ambulation Index indicate the status of the disease at the start of the treatment as determines by the Weiner protocol. None of the patients tested showed further progression of the disease beyond their original status for the periods of time listed in the last column.

I claim:

1. A method of treating demyelinating diseases of central or peripheral origin to retard their progression in a patient afflicted with such a disease which comprises administering to such a patient in one or more dosage units a composition consisting essentially of an inert excipient and an amount of colchicine or colchiceine which is effective to provide the active ingredient at a dosage of from about 0.02 to 0.04 mg/kg of body weight per day.

2. A method as in claim 1 wherein the active ingredient is colchicine.

3. A method as in claim 2 wherein the disease is multiple sclerosis.

* * * * *